United States Patent
Ito et al.

(10) Patent No.: US 10,448,537 B2
(45) Date of Patent: Oct. 15, 2019

(54) POWER SUPPLY DEVICE, PHOTOCHEMICAL REACTION DEVICE AND METHOD IN WHICH SAME IS USED, AND LACTAM PRODUCTION METHOD

(71) Applicant: TORAY INDUSTRIES, INC., Tokyo (JP)

(72) Inventors: Hiroyasu Ito, Nagoya (JP); Fumikatsu Ohno, Otsu (JP); Toru Takahashi, Otsu (JP); Fumio Fukuda, Tokai (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 15/580,875

(22) PCT Filed: Jun. 6, 2016

(86) PCT No.: PCT/JP2016/066715
§ 371 (c)(1),
(2) Date: Dec. 8, 2017

(87) PCT Pub. No.: WO2016/199706
PCT Pub. Date: Dec. 15, 2016

(65) Prior Publication Data
US 2018/0179148 A1   Jun. 28, 2018

(30) Foreign Application Priority Data
Jun. 11, 2015 (JP) .................. 2015-118229

(51) Int. Cl.
*H05K 7/20* (2006.01)
*C07C 249/04* (2006.01)
(Continued)

(52) U.S. Cl.
CPC ............. *H05K 7/20* (2013.01); *C07C 249/04* (2013.01); *C07C 251/44* (2013.01);
(Continued)

(58) Field of Classification Search
CPC ...................... H05K 7/20927; H01F 2027/406
(Continued)

(56) References Cited

U.S. PATENT DOCUMENTS 8,067,778 B2 * 11/2011 Bae .................. H01L 33/56
257/100
8,324,595 B2 * 12/2012 Takahashi .............. A01K 63/04
210/748.11
(Continued)

FOREIGN PATENT DOCUMENTS

JP        10209359 A     8/1998
JP        2012149055 A   8/2012
(Continued)

OTHER PUBLICATIONS

International Search Report and Written Opinion for International Application No. PCT/JP2016/066715, dated Aug. 9, 2016—7 Pages.

*Primary Examiner* — Kyle J Moody
(74) *Attorney, Agent, or Firm* — RatnerPrestia

(57) ABSTRACT

Provided is a power supply device, provided for a light source device which has a plurality of light-emitting bodies. The power supply device includes a circuit for controlling a current supplied to the light-emitting body. The power supply device also includes a control circuit for controlling a current from a power supply source, the control circuit being disposed at the central portion of the light source device. The power supply device additionally includes a cooling component capable of cooling surroundings by channeling a refrigerant, where the cooling component is provided on a back side of the light-emitting body. The power supply device also includes a heat transfer component connecting the cooling component and the control circuit to each other. The power supply device further includes an insulating component interposed between the heat transfer
(Continued)

11 Power supply device
12 Circuit board
13 Choke coil
14 Control-circuit-cooling member constituting part of heatsink
15 Member constituting part of heatsink
16 Heat transfer member
17 Insulator
18 Spring member
19 Spring force adjustment screw component and the control circuit at a state in contact with both.

18 Claims, 4 Drawing Sheets

(51) Int. Cl.
    *C07C 251/44* (2006.01)
    *F21V 29/503* (2015.01)
    *F21V 29/508* (2015.01)
    *F21V 29/56* (2015.01)
    *F21V 29/70* (2015.01)
    *C07D 201/04* (2006.01)
    *H05B 33/08* (2006.01)

(52) U.S. Cl.
    CPC ......... *C07D 201/04* (2013.01); *F21V 29/503* (2015.01); *F21V 29/508* (2015.01); *F21V 29/56* (2015.01); *F21V 29/70* (2015.01); *H05B 33/0803* (2013.01); *B01J 2219/0877* (2013.01)

(58) Field of Classification Search
    USPC .......................................................... 363/141
    See application file for complete search history.

(56) References Cited

U.S. PATENT DOCUMENTS

| | | | |
|---|---|---|---|
| 2011/0074296 A1* | 3/2011 | Shen | F21V 3/00 |
| | | | 315/112 |
| 2013/0050952 A1 | 2/2013 | Sone et al. | |
| 2016/0377391 A1* | 12/2016 | Rubtsov | F41H 13/0087 |
| | | | 315/297 |
| 2017/0238381 A1* | 8/2017 | Ohno | H05B 33/0815 |
| | | | 204/157.71 |
| 2017/0305851 A1* | 10/2017 | Uchiumi | B01J 19/127 |
| 2017/0365536 A1* | 12/2017 | Amo | H05K 7/20927 |

FOREIGN PATENT DOCUMENTS

| | | |
|---|---|---|
| JP | 2013051320 A | 3/2013 |
| JP | 2013200944 A | 10/2013 |
| JP | 2014093427 A | 5/2014 |

* cited by examiner

1 Light source device
2 Light-emitting body
3 Light transmitting container
4 Control circuit cooling heatsink
5 Cooling water
6 Heatsink
7 Control circuit
8 Insulator
9 Heat transfer member 11 Power supply device
12 Circuit board
13 Choke coil
14 Control-circuit-cooling member constituting part of heatsink
15 Member constituting part of heatsink
16 Heat transfer member
17 Insulator
18 Spring member
19 Spring force adjustment screw

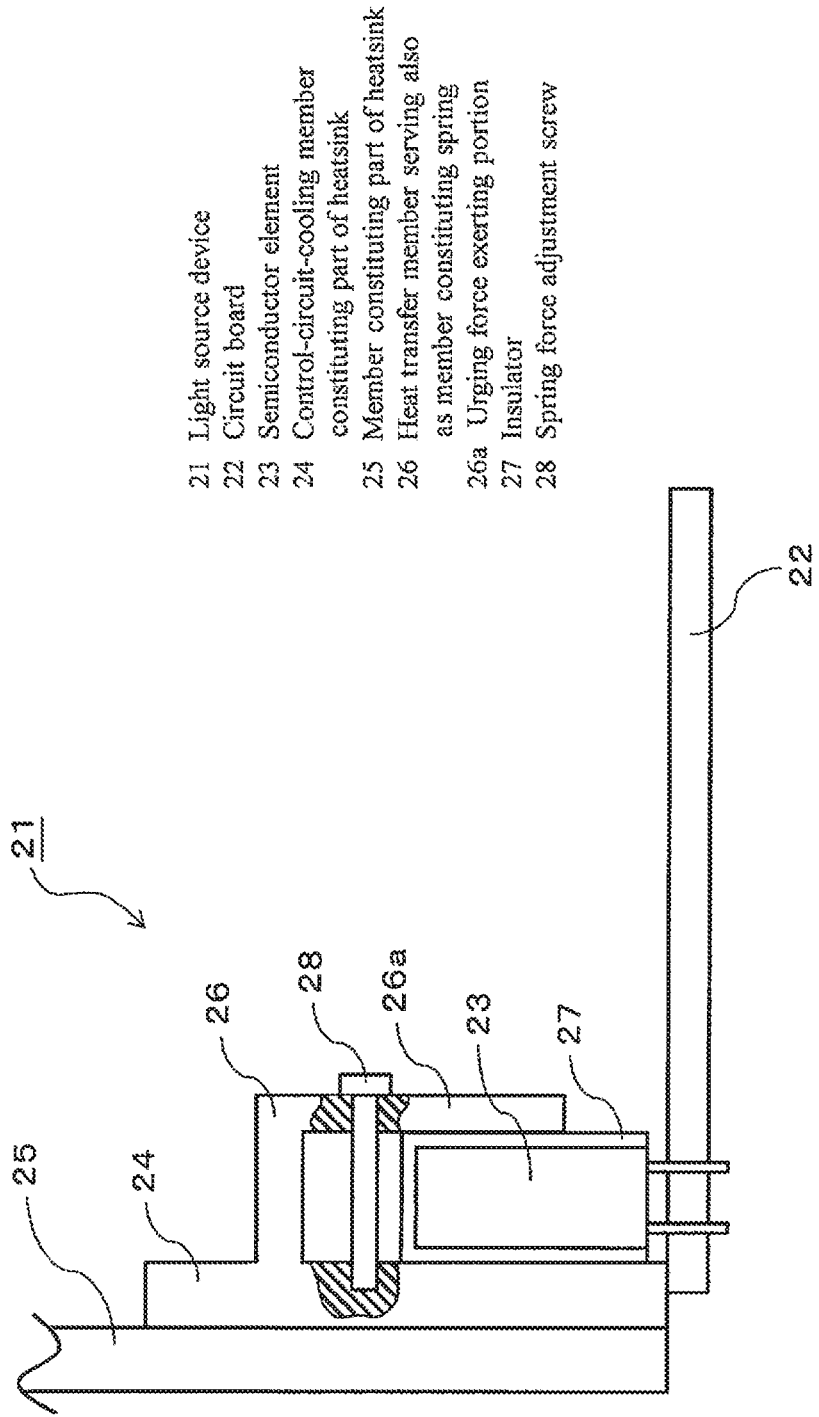

US 10,448,537 B2

POWER SUPPLY DEVICE, PHOTOCHEMICAL REACTION DEVICE AND METHOD IN WHICH SAME IS USED, AND LACTAM PRODUCTION METHOD

CROSS REFERENCE TO RELATED APPLICATIONS

This is the U.S. National Phase application of PCT/JP2016/066715, filed Jun. 6, 2016, which claims priority to Japanese Patent Application No. 2015-118229, filed Jun. 11, 2015, the disclosures of these applications being incorporated herein by reference in their entireties for all purposes.

TECHNICAL FIELD OF THE INVENTION

The present invention relates to a power supply device having a control circuit for controlling a current from a power supply source, and specifically, to a power supply device capable of suppressing a temperature rise of a control circuit, photochemical reaction device and method using the power supply device, and a method for producing lactam using the photochemical reaction method.

BACKGROUND OF THE INVENTION

In a power supply device having a control circuit for controlling a current from a power supply source, it is frequently performed to mount electric and electronic components such as a switching element using a semiconductor element and a reactor using a choke coil on the control circuit. However, in such electric and electronic components, usually, if the temperature exceeds a certain temperature, there is a possibility that the operation becomes unstable or the lifespan decreases. Such a problem of temperature rise is likely to occur, in particular, in case where a large heat radiation space from these electric and electronic components cannot be taken, for example, in case where compactification of the whole apparatus is required and a large heat radiation space for a control circuit or a power supply device incorporated therewith cannot be taken.

For example, in a power supply device for a light source using a light emitting diode (hereinafter, sometimes abbreviated as "LED"), as LED light sources become more powerful and highly integrated, there is a problem that a space volume required for suppressing the calorific value of the LED elements and the power supply control circuit decreases and the temperature of electric and electronic components such as a choke coil or semiconductor elements constituting the power supply control circuit elevates up to an undesired level. Since lifespan of electric and electronic components is greatly affected by heat, in an LED light source required with long lifespan, it is necessary to efficiently cool the electric and electronic components in order to suppress such a temperature rise, and particularly for a large capacity LEI) light source, that necessity increases.

For the large capacity LED light source device as described above, Patent document 1 proposes a light source device wherein leakage of a coolant from a cooling system for cooling the light source device is detected, and damage to a light source or a power source due to adhesion of the coolant can be prevented, but it is not mentioned to efficiently cool the electric and electronic components in order to suppress a temperature rise of a power supply control circuit, it is still insufficient from the viewpoint of securing stable operation of the control circuit and making the lifespan longer.

Patent Documents

Patent document 1: JP-A-2013-200944

SUMMARY OF THE INVENTION

Accordingly, in view of the above-described problems, an object of the present invention is to provide a power supply device having a control circuit for controlling a current from a power supply source, which has a structure capable of adequately suppressing a temperature rise of the power supply device, and in particular, to provide a power supply device suitable for a large capacity LED light source. Particularly, in industrial discharge tubes and the like, an extraordinarily large light quantity is required, while it is necessary to increase the absolute number of the LEDs, in order to apply to existing facilities, a plurality of LEDs are to be intensively arranged, and even in case where it is more difficult to adequately suppress the temperature rise, a power supply device capable of being stably controlled is required.

To achieve the above-described object, a power supply device according to one aspect of the present invention comprises: a control circuit for controlling a current from a power supply source; a cooling means capable of cooling surroundings by channeling a refrigerant; a heat transfer means connecting the cooling means and the control circuit to each other; and an insulating means interposed between the heat transfer means and the control circuit at a state in contact with both.

In such a power supply device according to the present invention, when the current from the power supply source is increased, although there is a possibility that the control circuit mounted with electric and electronic components generates heat, since a heat transfer route, formed by the heat transfer means connected to the cooling means and the control circuit and the insulating means interposed between the heat transfer means and the control circuit at a state in contact with both, is formed between the cooling means capable of cooling surroundings by channeling a refrigerant and the control circuit, the heated control circuit is efficiently cooled through this heat transfer route, and the amount of heat generation is suppressed to an appropriate level or less. In particular, because the control circuit is brought into contact with the insulating means and the insulating means is brought into contact with the heat transfer means, the heat transfer route capable of transferring heat very efficiently can be formed from the control circuit to the cooling means is formed, and the control circuit heated can be effectively cooled. As a result, while a necessary insulation state is ensured by the insulating means, an excessive temperature rise of the control circuit can be prevented, the function of the control circuit can be stably maintained, and it can be achieved to make the lifespan of electric and electronic components longer.

In the above-described power supply device according to the present invention, an embodiment can be employed wherein the control circuit comprises a circuit component comprising at least a switching element or/and a reactor, and at least the insulating means is in contact with the circuit component. Since the switching element or the reactor is a circuit component easy to generate heat when a large current flows easy to cause functional deterioration when an excessive temperature rise occurs, by cooling such a circuit component intensively among the parts in the control circuits, the function of the control circuit can be maintained more stably.

Further, although the above-described cooling means is not particularly limited as long as it is a means capable of cooling the surroundings by channeling of the refrigerant, and its structure is also not particularly limited, if the cooling means comprises a cooling water channeling passage, since it is possible to employ a general technology for a structure of the channeling of cooling water and a control of its flow rate, it is possible to easily apply it to the power supply device according to the present invention. Moreover, a high cooling performance can be achieved by an adequate design of the channeling passage and an adequate control of the flow rate of the cooling water.

Further, although the above-described heat transfer means also is not particularly limited as long as it is a means connecting the cooling means and the control circuit and capable of enabling heat transfer therebetween, and its structure also is not particularly limited, in order to obtain a heat transfer performance as high as possible, ultimately a cooling performance as high as possible, it is preferred that it is made of a material having a high thermal conductivity coefficient. For example, it is preferred that the heat transfer means comprises a metal member having a thermal conductivity coefficient of 2 W/m·K or more. By having a thermal conductivity coefficient of 2 W/m·K or more, it becomes possible to obtain a sufficiently high heat transfer performance, ultimately, a sufficiently high cooling performance.

Further, although the above-described insulating means also is not particularly limited as long as it can ensure a necessary insulation performance with respect to the control circuit and can be interposed between the heat transfer means and the control circuit at a state of being in contact with both, and its structure also is not particularly limited, in order to obtain a heat transfer performance as high as possible, ultimately a cooling performance as high as possible, it is preferred that it is made of a material having a high thermal conductivity coefficient. Because of an insulating means, it cannot be composed of a metal member having a conductivity, but for example, it is preferred that the insulating means comprises a sheet-like member having a thermal conductivity coefficient of 0.4 W/m·K or more. Since the insulating means may be relatively thin as long as insulation property is secured, by having a heat conduction coefficient of 0.4 W/m·K or more, it becomes possible to obtain a sufficiently high heat transfer performance, ultimately, a sufficiently high cooling performance. As a sheet-like member having such a heat conduction coefficient, for example, a sheet-like member made of silicon can be exemplified.

Further, in the power supply device according to the present invention, in order to maintain a higher cooling performance, it is preferred that the heat transfer means connected to the cooling means is maintained at a state always in contact with the control circuit side via the insulating means. For that, it is preferred that the power supply device according to the present invention further comprises an urging means capable of urging the heat transfer means to the side of the control circuit. Since it becomes possible to always urge the heat transfer means toward the control circuit side by the urging means, it becomes possible to always maintain a desired contact state in the heat transfer route, thereby obtaining an excellent cooling performance. Such an urging means may be constituted by means such as a separately provided spring member or the like, or may also be constituted integrally with the heat transfer means by forming a part of the heat transfer means as a portion having a spring function.

It is preferred that an urging force adjustment means for adjusting the urging force of the urging means is attached to the above-described urging means. By adjusting the urging force by the urging force adjustment means, it is possible to maintain the contact state at a more stable and more suitable contact pressure of the contact part. Such an urging force adjustment means is not particularly limited, and a means having an arbitrary urging force adjusting function can be applied, and for example, it is possible to form it by an adjustment screw capable of adjusting the posture and the pressing force of the spring member or the part having the spring function as described above.

The power supply device according to the present invention as described above can be applied to a power supply device in any field having a control circuit for controlling the current from the power supply source, and in particular, it is useful as a power supply device in which the control circuit comprises a circuit for controlling a current supplied to a light-emitting body using a plurality of light emitting diodes.

In case of thus being applied as a power supply device for a light source having a light-emitting body using light emitting diodes, it is preferred that the above-described cooling means is provided on the back side of the light-emitting body. Namely, it is preferred that the cooling means is configured so as not to obstruct the light irradiation route on the front side of the light-emitting body.

In the light source having such a light-emitting body, the irradiated light from the light-emitting body can be used, for example, for a photochemical reaction. For example, as described later, the destination of the light from the light-emitting body is a cycloalkane, and it can be used in a photochemical reaction process for preparing cycloalkanone oxime by the light irradiation. Lactam can be produced using cycloalkanone oxime prepared in the photochemical reaction process.

A photochemical reaction device according to an aspect of the present invention comprises a photoirradiation device having a light emitting diode group connected to the power supply device as described above, By applying the above-described power supply device, it becomes possible to stably and continuously illuminate the light emitting diode group, and it becomes possible to perform a desired photochemical reaction due to the photoirradiation device.

Further, a photochemical reaction method according to another aspect of the present invention comprises a method characterized by using such a photochemical reaction device.

This photochemical reaction method according to the present invention can be applied to any of photochemical reactions required to stably and continuously illuminate a large-capacity light emitting diode group, for example, to a photochemical reaction in which the destination of photoirradiation is a liquid, and the composition of the liquid contains at least a carbon atom. As the liquid as the destination of photoirradiation, for example, a cycloalkane can be exemplified. As the cycloalkane, for example, cyclohexane or cyclododecane can be exemplified. The photochemical reaction method according to the present invention is suitable to, in particular, a photochemical reaction wherein a cycloalkanone oxime is produced by performing photoirradiation to such a cycloalkane and a photo nitrosating agent. As the photo nitrosating agent, for example, nitrosyl chloride or tfichloronitrosomethane can be exemplified.

A method for producing a lactam according to an aspect of the present invention is characterized by converting the cycloalkanone oxime produced by the photochemical reaction method as described above succeedingly to lactam.

Thus, in the power supply device according to the present invention, since it is possible to efficiently constitute a heat transfer route between the cooling means and the control circuit, and to effectively dissipate heat from the heated control circuit and adequately cool the control circuit, an excessive temperature rise of the control circuit can be prevented, the function of the control circuit can be stably maintained, and the lifespan of the electric and electronic components mounted on the control circuit can be made longer. By applying this power supply device according to the present invention, it becomes possible to construct a high power and highly integrated LED light source device, and it becomes possible to operate the light source device stably for a long time. Therefore, this power supply device is particularly effective for the photochemical reaction device and method which irradiates light with a large capacity light emitting diode group, and furthermore, it can contribute to stabilize the method for producing lactam using cycloalkanone oxime produced by the photochemical reaction method.

BRIEF DESCRIPTION OF THE DRAWINGS

FIG. 4 is a schematic diagram showing another configuration example of a power supply device in the light source device shown in FIG. 1.

DETAILED DESCRIPTION OF EMBODIMENTS OF THE INVENTION

Hereinafter, embodiments of the present invention will be explained referring to figures.

Figure 1:
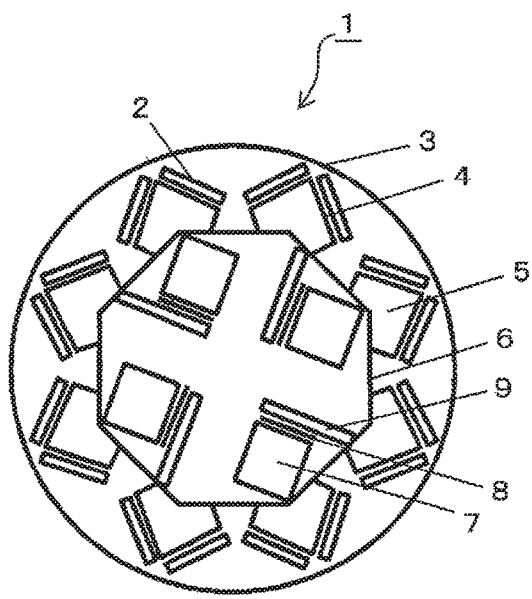
FIG. 1 is a schematic cross-sectional view of a light source device using a power supply device according to an embodiment of the present invention.

FIG. 1 exemplifies a case where a power supply device according to an embodiment of the present invention is applied to a light source device, and shows a schematic cross section of the light source device. The light source device 1 shown in FIG. 1 has a plurality of light-emitting bodies 2 on each of which, for example, a large number of light emitting diodes are mounted, and their entirety is covered with a cylindrical light transmitting container 3. The number of mounted light emitting diodes in each light-emitting body 2 may be appropriately determined depending upon the use of the light source device 1. In the illustrated example, each light-emitting body 2 is mounted on two surfaces of the outer surface of a control circuit cooling heat sink 4 as a cooling means having a cooling water channeling passage, and a plurality of mounted light-emitting bodies 2 are formed into a star shape as the whole cross-sectional shape. Each control circuit cooling heatsink 4 is provided on the back surface side of each light-emitting body 2 and it serves also as a cooling means for light-emitting body 2. Cooling water 5 as a refrigerant is channeled in each control circuit cooling heatsink 4.

At the central portion of the light source device 1, a heatsink 6 is formed as a cooling means capable of cooling approximately the whole of the light source device 1, and this heatsink 6 is also configured as a cooling means having a cooling water channeling passage. Further, at the central portion of the light source device 1, a control circuit 7 for controlling current from a power supply source (not shown) is disposed so as to be able to be cooled by the heatsink 6, at a plural form in correspondence with the number of groups of the light-emitting bodies 2 (four in the illustrated example). From each control circuit 7, a heat transfer member 9 as a heat transfer means forming a heat transfer route extending up to each control circuit cooling heatsink 4 is provided interposing an insulator 8 as an insulating means made of a sheet-like member having a thermal conductivity coefficient of 0.4 W/m·K or more. This heat transfer member 9 is made of a metal member having a thermal conductivity coefficient of 2 W/m·K or more.

Figure 2:
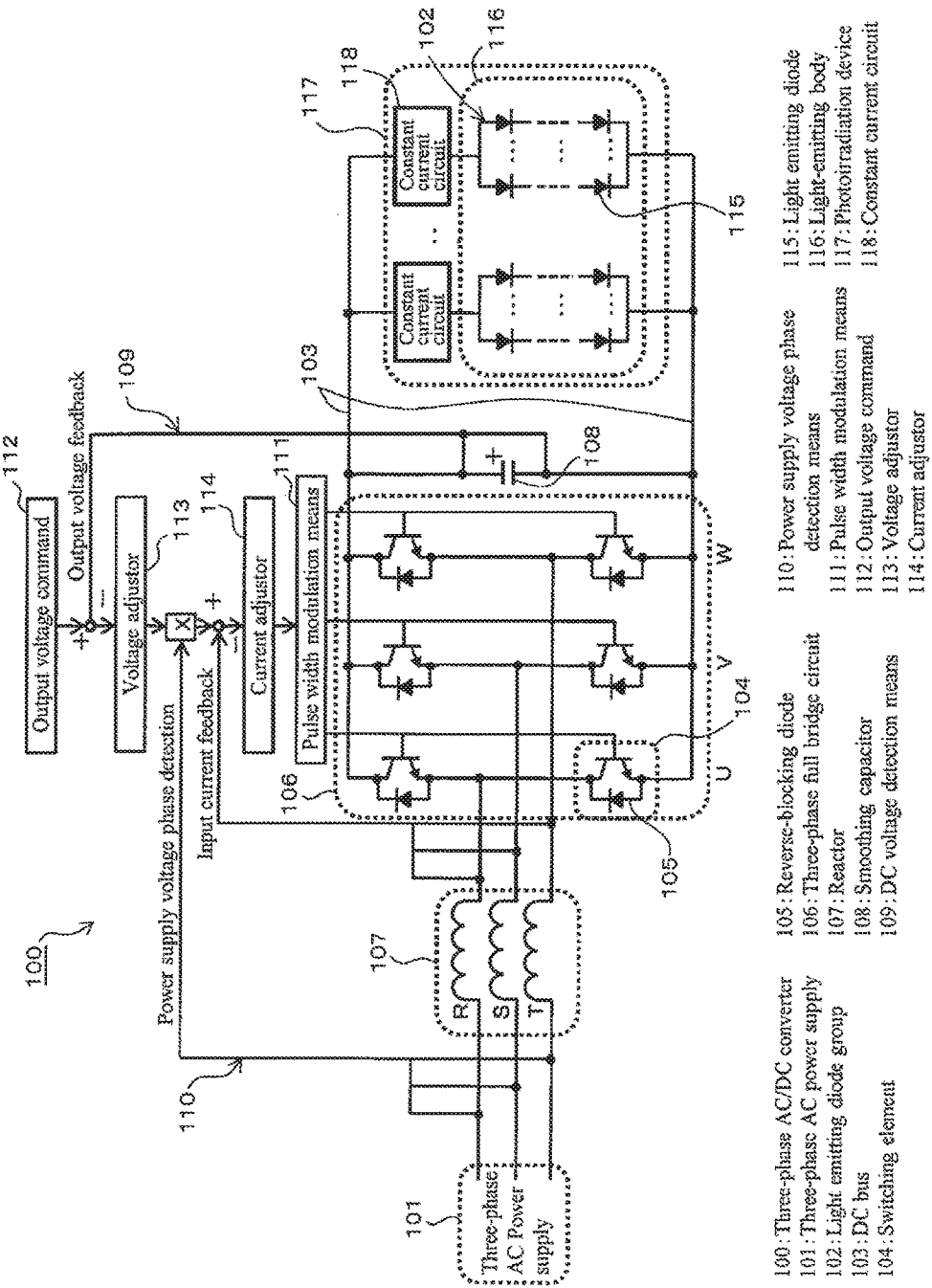
FIG. 2 is a circuit diagram showing a configuration example of an entire circuit of the light source device shown in FIG. 1.

FIG. 2 shows a configuration example of an entire circuit including a control circuit for controlling a current from a power supply source of the light source device 1 having the above-described light-emitting body mounted with the light emitting diode groups. FIG. 2 shows a configuration example of a circuit in case where a three-phase AC/DC converter is configured. The three-phase AC/DC converter 100 shown in FIG. 2 is a three-phase AC/DC converter, for example, incorporated into a power supply circuit disposed between a three-phase AC power supply 101 and light emitting diode groups 102, in order to drive the light emitting diode groups of 3 kw or more with a single unit. The three-phase AC/DC converter 100 has DC buses 103 connected to the light emitting diode groups 102; a three-phase full bridge circuit 106 (bridge circuit of three phases U, V and W) in which pairs of switching elements 104, in each of which a pair of switching elements 104 are connected in series, are connected in parallel between the DC buses 103 by pairs for three phases of the three-phase AC power supply 101, and each switching element 104 has a reverse-blocking diode 105 connected thereto in parallel; a reactor 107 provided between the three-phase full bridge circuit 106 and the three-phase AC power supply 101 for connecting a connection portion between switching elements 104 in each pair of switching elements 104 and a corresponding phase (phase R, S or T) of the three-phase AC power supply 101; a smoothing capacitor 108 connected between the DC buses 103 on an output side of the three-phase full bridge circuit 106; a DC voltage detection means 109 for detecting an output voltage between the DC buses 103; a power supply voltage phase detection means 110 for detecting a power supply voltage phase of the three-phase AC power supply 101; and a pulse width modulation means (PWM means) 111 connected to each of the switching elements 104 for outputting a pulse width modulation signal for controlling each of the switching elements 104. The pulse width modulation means 111 outputs the pulse width modulation signal to each of the switching elements 104 based on the power supply voltage phase detected by the power supply voltage phase detection means 110 and the output voltage between the DC buses 103 detected by the DC voltage detection means 109.

In the above-described configuration example, the output voltage between the DC buses 103 detected by the DC voltage detection means 109 and fed back and a preset output voltage command 112 are compared, and adjusted by a voltage adjustor 113. The current based on the phase of the adjusted voltage and the power supply voltage phase detected by the power supply voltage phase detection means 110 is compared with the input current fed back from the input side of the three-phase full bridge circuit 106, and after the current is adjusted by a current adjustor 114, it is subjected to the pulse width modulation control due to the pulse width modulation means 111.

Further, a plurality of light emitting diodes 115 are combined and connected to form one light emitting diode group 102, a plurality of light emitting diode groups 102 are provided in parallel, and a large-scale light-emitting body 116 is constituted. A device having this light-emitting body 116 is configured as a photoirradiation device 117 used in, for example, a photochemical reaction device. In this photoirradiation device 117, a plurality of constant current circuits 118 for controlling the currents to the respective light emitting diode groups 102 to be constant are provided in parallel relatively to the output side of the three-phase full bridge circuits 106.

In the three-phase AC/DC converter 100 thus constructed, since a converter comprising the three-phase full bridge circuit 106 combined with switching elements 104 capable of being performed with PWM control is formed on the converting section from three-phase AC to DC, it becomes possible to correct the high frequency and noise on the secondary side, that is, the output side (DC buses 103 side) of the three-phase full bridge circuit 106, and the high frequency generated on the primary side, and make it a power supply waveform having no distortion, and the voltage drop on the primary side, that is, on the input side of the 3-phase full bridge circuit 106 (reactor 107 side) is suppressed. Further, since the smoothing capacitor 108 is also added, the DC voltage on the side of the DC buses 103 is controlled at a constant voltage with a smooth waveform, and by applying the PWM control to the three-phase full bridge circuit 106, a stable voltage supply with less fluctuation becomes possible.

As aforementioned, in case where the above-described control circuit has at least a switching element or/and a circuit component comprising a reactor, since these switching element and reactor are circuit components which are liable to generate heat when a large current flows, and are liable to reduce in function when an excessive temperature rise occurs, the function of the control circuit is maintained more stably by being intensively cooled with such circuit components in the control circuit.

Figure 3:
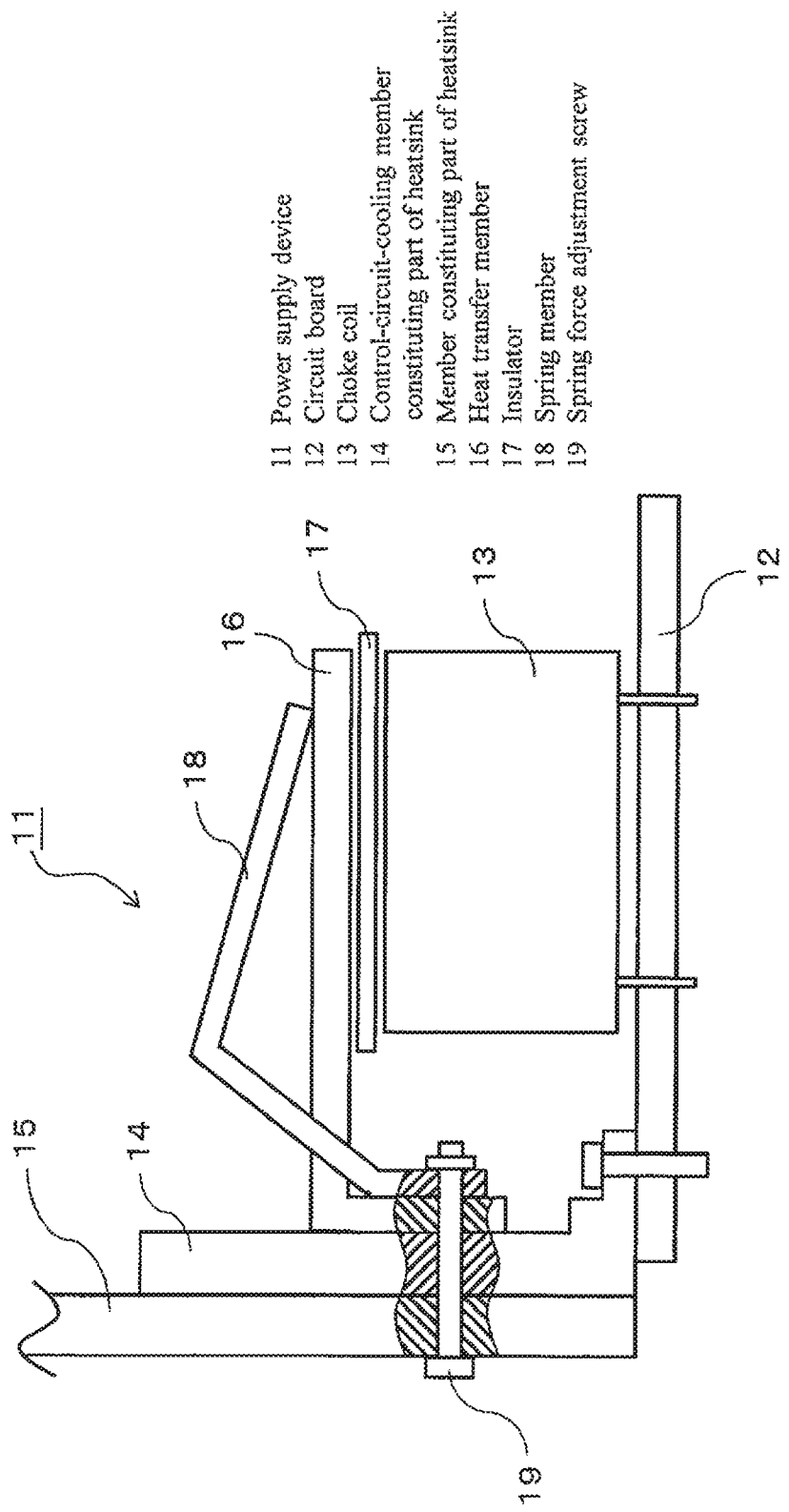
FIG. 3 is a schematic diagram showing a configuration example of a power supply device in the light source device shown in FIG. 1.

Examples of the configuration of the power supply device according to the present invention used for the light source device 1 as shown in FIG. 1 are exemplified in FIGS. 3 and 4. In a power supply device 11 shown in FIG. 3, symbol 12 indicates a circuit board of one control circuit 7 in the light source device 1 as shown in FIG. 1, and a portion mounted with a choke coil 13 constituting a reactor is exemplified on the circuit board 12. Symbol 14 indicates a control-circuit-cooling member constituting part of heatsink which forms a part of one control circuit cooling heatsink 4 in the light source device 1 as shown in FIG. 1, and symbol 15 indicates a member constituting part of heatsink for forming a part of heatsink 6 as the cooling means capable of cooling approximately the whole of the light source device 1 in the light source device 1 as shown in FIG. 1. In this embodiment, a part of the control-circuit-cooling member constituting part of heatsink 14 as a cooling means is connected to the circuit board 12. Between the control-circuit-cooling member constituting part of heatsink 14 as a cooling means and the choke coil 13 as a part of the control circuit, provided is a heat transfer member 16 as a heat transfer means having a U-shaped cross section (for example, an aluminum heat transfer member as a heat transfer means comprising a metal member having a thermal conductivity coefficient of 2 W/m·K or more), and this heat transfer member 16 corresponds to the heat transfer member 9 in FIG. 1. Between the heat transfer member 16 and the choke coil 13, an insulator 17 as a sheet-like insulating means (for example, a silicon insulator as an insulating means comprising a sheet-like member having a thermal conductivity coefficient of 0.4 W/m·K or more) is interposed at a state of being in contact with both of them, and this insulator 17 corresponds to the insulator 8 in FIG. 1.

The heat transfer member 16 is connected to the choke coil 13 (the top surface of the choke coil 13) via the insulator 17, and in order to make the contact state at this portion securer, in this embodiment, a spring member 18 is provided as an urging means capable of urging the heat transfer member 16 to the choke coil 13 side toward the lower direction in FIG. 3. The urging force of this spring member 18 can be appropriately adjusted by a spring force adjustment screw 19 as an urging force adjustment means.

In the power supply device 11 configured as described above, even in case where the choke coil 13 constituting a part of the control circuit 7 generates heat and the temperature is about to rise, since the heat of the choke coil 13 is dissipated to the control-circuit-cooling member constituting part of heatsink 14 and further dissipated to the member constituting part of heatsink 15 through the insulator 17 which is brought into direct contact with the choke coil 13 and the heat transfer route which is formed by the heat transfer member 16 whose contact pressure to the choke coil 13 side is adjusted by the spring member 18 whose urging force is adjusted by the spring force adjustment screw 19 via the insulator 17, the choke coil 13 is efficiently cooled. As a result, while the necessary insulation state is secured by the insulator 17, the temperature rise of the choke coil 13 is adequately suppressed, and the stable performance of the choke coil 13 is maintained as well as the long lifespan thereof becomes possible.

In a power supply device 21 shown in FIG. 4, on a circuit board 22 of one control circuit 7 in the light source device 1 as shown in FIG. 1, a portion on which a semiconductor element 23 constituting a part of the control circuit 7 is mounted is exemplified. Symbol 24 indicates a control-circuit-cooling member constituting part of heatsink forming a part of one control circuit cooling heatsink 4 in the light source device 1 as shown in FIG. 1, and symbol 25 indicates a member constituting part of heatsink forming a part of the heatsink 6 as the cooling means capable of cooling approximately the whole of the light source device 1 in the light source device 1 as shown in FIG. 1. In this embodiment, a part of the control-circuit-cooling member constituting part of heatsink 24 as the cooling means is connected to the circuit board 22. Between the control-circuit-cooling member constituting part of heatsink 24 as the cooling means and the semiconductor element 23 as a part of the control circuit, provided is a heat transfer member 26 as a heat transfer member having a L-shaped cross section (for example, an aluminum heat transfer member as a heat transfer means comprising a metal member having a thermal conductivity coefficient of 2 W/m·K or more), and this heat transfer member 26, in the illustrated example, is formed integrally with the above-described control-circuit-cooling member constituting part of heatsink 24 as well as is constituted as a heat transfer member serving also as spring member which is formed integrally with an urging force exerting portion 26a capable of exerting an urging force toward the semiconductor element 23 side, similarly in the spring member in FIG. 3. Between the heat transfer member serving also as spring member 26 and the semiconductor element 23, in the illustrated example, further between the semiconductor element 23 and the control-circuit-cooling member constituting part of heatsink 24, an insulator 27 as a sheet-like insulating means, which is provided so as to cover the semiconductor element 23, (for example, a silicon insulator as an insulating means comprising a sheet-like member having a thermal conductivity coefficient of 0.4 W/m·K or more) is interposed at a state of being in contact with both of the urging force exerting portion 26a and the control-circuit-cooling member constituting part of heatsink 24, and this insulator 27 corresponds to the insulator 8 in FIG. 1.

Although the urging force exerting portion 26a of the heat transfer member serving also as spring member 26 is connected to the semiconductor element 23 via the insulator 27, in order to make the contact state at this portion securer, in this embodiment, the urging force of the urging force exerting portion 26a toward the semiconductor element 23 side toward the directions of the right and left sides in FIG. 4 can be appropriately adjusted by the spring force adjustment screw 28 as urging force adjustment means. In the illustrated example, this spring force adjustment screw 28 can simultaneously adjust the contact pressure between the control-circuit-cooling member constituting part of heatsink 24 and the semiconductor element 23 via the insulator 27.

In the power supply device 21 configured as described above, even in case where the semiconductor element 23 constituting a part of the control circuit 7 generates heat and the temperature is about to rise, since the heat of the semiconductor element 23 is dissipated to the control-circuit-cooling member constituting part of heatsink 24 and further dissipated to the member constituting part of heatsink 25 through the insulator 27 which is brought into direct contact with the semiconductor element 23 and the heat transfer route which is formed by the urging force exerting portion 26a of the heat transfer member serving also as spring member 26 whose urging force is adjusted by the spring force adjustment screw 28 via the insulator 27, the semiconductor element 23 is efficiently cooled. Further, in the illustrated example, since a heat transfer route for radiating heat directly to the side of the control-circuit-cooling member constituting part of heatsink 24 through the insulator 27 directly contacted to the semiconductor element 23 is also formed, the semiconductor element 23 is cooled more efficiently. As a result, while the necessary insulation state is secured by the insulator 27, the temperature rise of the semiconductor element 23 is adequately suppressed, and the stable performance of the semiconductor element 23 is maintained as well as the long lifespan thereof becomes possible.

Where, in the embodiments shown in FIGS. 3 and 4, although the choke coil 13 and the semiconductor element 23 are exemplified as the electric and electronic components constituting a part of the control circuit, the electric and electronic components constituting a part of the control circuit in the present invention are not limited thereto, and any electric and electronic component with a possibility of generating heat becomes an object of cooling according to the present invention, for example, a capacitor and the like also becomes an object of the cooling.

As aforementioned, the power supply device according to the present invention can be applied to a power supply device of any field having a control circuit for controlling a current from a power supply source, and in particular, it is useful as a power supply device in which its control circuit comprises a circuit controlling a current supplied to a light-emitting body using a plurality of light emitting diodes. Namely, it is useful as a power supply device for the light source device 1 as shown in FIG. 1, and in particular, as shown in FIG. 1, an embodiment is preferred wherein a cooling means is provided on the back surface side of the light-emitting body 2.

In the present invention, a power supply device can be provided which can be used to drive a group of light emitting diodes with a large capacity, particularly 3 kW or more, preferably 10 kW or more and 100 kw or less, with a single power supply device, and which can light the light emitting diodes stably. By using the power supply device according to the present invention, it becomes possible to operate a light source device highly integrated with light emitting diodes of 10,000 or more, preferably 20,000 or more. The upper limit of the number of highly integrated light emitting diodes is about 100,000. In the light source device using the power supply device according to the present invention, further by suppressing the temperature rise of the control circuit required to light the large-capacity light emitting diode group, it is possible to drive the light emitting diode group stably for a long time and to extend the lifespan of the light emitting diodes.

Furthermore, by using the power supply device according to the present invention, it becomes possible to stably control a highly integrated light emitting diode group, and it becomes possible to drive a light emitting diode group integrated at a density of 1 diode/cm$^2$ or more and 5 diodes/cm$^2$ or less. The lower limit of the degree of integration of light emitting diodes is preferably 2/cm$^2$ or more, more preferably 3/cm$^2$ or more. By such a configuration, it becomes possible to further increase the density and the capacity of the light emitting diode group.

In the light source device 1 provided with the light-emitting body as described above, it can be applied to any photochemical reaction particularly required to stably and continuously light up a large-capacity light emitting diode group. For example, in the photochemical reaction method, the destination of the photoirradiation can be set to be a liquid which contains carbon atoms. Namely, in the photochemical reaction method according to the present invention, at least one destination of the photoirradiation may be a raw material system composed of a liquid. The liquid served as a raw material is not particularly restricted as long as it is a liquid containing carbon atoms, and as a reaction liquid, a flammable liquid, for example, hydrocarbons such as alkane and cycloalkane can be exemplified.

Where, although the above-described cycloalkane is not particularly limited in the number of carbon atoms, for example, cyclopropane, cyclobutane, cyclopentane, cyclohexane, cycloheptane, cyclooctane, cyclononane, cyclodecane, cycloundecane, and cyclododecane are preferred. In particular, cyclohexane as a raw material of lactam and cyclododecane as a raw material of lauryl lactam are preferred.

Using the above-described cycloalkane and a photo nitrosating agent, cycloalkanone oxime is obtained by photochemical reaction due to the photo irradiation of light emitting diodes. As the photo nitrosating agent, for example, nitrosyl chloride or a mixed gas of nitrosyl chloride and hydrogen chloride is preferred. Besides, since any of the mixed gas of nitric monoxide and chlorine, the mixed gas of nitric monoxide, chlorine and hydrogen chloride, the mixed gas of nitrose gas and chlorine, etc. acts as nitrosyl chloride in the photochemical reaction system, it is not limited to these supply forms of the nitrosating agent. Further, trichloronitrosomethane obtained by photochemical reaction of nitrosyl chloride and chloroform may be used as a nitrosating agent. In case where the photochemical reaction is carried out in the presence of hydrogen chloride, the cycloalkanone oxime becomes its hydrochloride, but it may be in the form of hydrochloride as it is.

By the above-described photochemical reaction, it is possible to obtain cycloalkanone oxime which depends upon the carbon number of the cycloalkane. For example, cyclohexanone oxime is obtained by photo nitrosating reaction with nitrosyl chloride using cyclohexane. Further, cyclododecanone oxime is obtained by photo nitrosating reaction with nitrosyl chloride using cyclododecane.

A lactam can be obtained by Beckmann rearrangement of the cycloalkanone oxime obtained by the photochemical reaction. For example, in the reaction of Beckmann rearrangement of cyclohexanone oxime, ε-caprolactam is obtained as shown by the following reaction formula [Chemical formula 1]. Further, ω-laurolactam is obtained in the reaction of Beckmann rearrangement of cyclododecanone oxime

[Chemical formula 1]

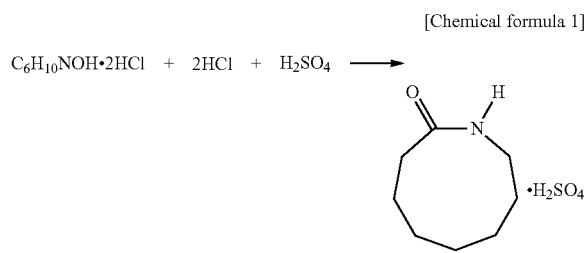

$C_6H_{10}NOH \cdot 2HCl + 2HCl + H_2SO_4 \longrightarrow$

Where, in the above description, although the embodiment of the present invention has been explained with reference to the light source device 1 shown in FIG. 1, this embodiment is shown as an example, and it is not intended to limit the scope of the present invention. It can be carried out in various forms, and can be appropriately simplified or changed without departing from the gist of the present invention. These embodiments and modifications thereof are also included in the scope of the present invention.

The power supply device according to the present invention can be applied to a power supply device in any field having a control circuit for controlling the current from the power supply source, and in particular, it is suitable as a power supply device for a light source device having a control circuit comprising a circuit for controlling a current supplied to a light-emitting body using a plurality of light emitting diodes. Such a power supply device for a light source device is suitable particularly for use in a photochemical reaction method, a photochemical reaction device, and a method for producing lactam using the photochemical reaction method.

EXPLANATION OF SYMBOLS

1: light source device
2: light-emitting body
3: light transmitting container
4: control circuit cooling heatsink
5: cooling water
6: heatsink
7: control circuit
8: insulator
9: heat transfer member
11, 21: power supply device
12, 22: circuit board
13: choke coil
14, 24: control-circuit-cooling member constituting part of heatsink
15, 25: member constituting part of heatsink
16: heat transfer member
17, 27: insulator
18: spring member
19, 28: spring force adjustment screw
23: semiconductor element
26: heat transfer member serving also as spring member
26a: urging force exerting portion
100: three-phase AC/DC converter
101: three-phase AC power supply
102: light emitting diode group
103: DC bus
104: switching element
105: reverse-blocking diode
106: three-phase full bridge circuit
107: reactor
108: smoothing capacitor
109: DC voltage detection means
110: power supply voltage phase detection means
111: pulse width modulation means
112: output voltage command.
113: voltage adjustor
114: current adjustor
115: light emitting diode
116: light-emitting body
117: photoirradiation device
118: constant current circuit

The invention claimed is:

1. A power supply device, provided for a light source device which has a plurality of light-emitting bodies on each of which a large number of light emitting diodes are mounted, an entirety of the plurality of light-emitting bodies being covered with a cylindrical light transmitting container, said power supply device comprising:
   a circuit for controlling a current supplied to the entirety of the plurality of light-emitting bodies;
   a control circuit for controlling a current from a power supply source, said control circuit being disposed at a central portion of said light source device;
   a cooling means capable of cooling surroundings by channeling a refrigerant, said cooling means being provided on a back side of the entirety of the plurality of the light-emitting bodies;
   a heat transfer means connecting said cooling means and said control circuit to each other; and
   an insulating means interposed between said heat transfer means and said control circuit at a state in contact with both,
   wherein
   the control circuit is positioned inside the power supply device and surrounded with the plurality of the light-emitting bodies, and
   the cooling means cools the control circuit via the heat transfer means and at a same time cools the entirety of the plurality of light-emitting bodies.

2. The power supply device according to claim 1, wherein said control circuit comprises a circuit component comprising at least a switching element or/and a reactor, and at least said insulating means is in contact with said circuit component.

3. The power supply device according to claim 1, wherein said cooling means comprises means having a cooling water channeling passage.

4. The power supply device according to claim 1, wherein said heat transfer means comprises a metal member having a thermal conductivity coefficient of 2 W/m·K or more.

5. The power supply device according to claim 1, wherein said insulating means comprises a sheet-like member having a thermal conductivity coefficient of 0.4 W/m·K or more.

6. The power supply device according to claim 1, further comprising an urging means capable of urging said heat transfer means to the side of said control circuit.

7. The power supply device according to claim 6, further comprising an urging force adjustment means for adjusting an urging force of said urging means.

8. The power supply device according to claim 7, wherein said urging force adjustment means comprises a spring member.

9. The power supply device according to claim 1, wherein said light-emitting body is one irradiated light of which is used for a photochemical reaction.

10. A photochemical reaction device comprising a photoirradiation device having a light emitting diode group connected to the power supply device according to claim 1.

11. A photochemical reaction method characterized by using the photochemical reaction device according to claim 10.

12. The photochemical reaction method according to claim 11, wherein a destination of photoirradiation is a liquid, and the composition of said liquid contains at least a carbon atom.

13. The photochemical reaction method according to claim 12, wherein said liquid as the destination of photoirradiation is a cycloalkane.

14. The photochemical reaction method according to claim 13, wherein said cycloalkane is cyclohexane or cyclododecane.

15. The photochemical reaction method according to claim 13, wherein a cycloalkanone oxime is produced by performing photoirradiation to said cycloalkane and a photo nitrosating agent.

16. The photochemical reaction method of claim 15, wherein said photo nitrosating agent is nitrosyl chloride or trichloronitrosomethane.

17. A method for producing a lactam characterized by converting cycloalkanone oxime produced by the photochemical reaction method according to claim 16 to lactam.

18. The power supply device according to claim 1, wherein said heat transfer means comprises a heat transfer member having a L-shaped cross section.

* * * * *